United States Patent [19]

de Vries

[11] Patent Number: 4,569,838

[45] Date of Patent: Feb. 11, 1986

[54] DENTIFRICE

[75] Inventor: Marijke S. de Vries, Upper Montclair, N.J.

[73] Assignee: Colgate-Palmolive Company, New York, N.Y.

[21] Appl. No.: 670,385

[22] Filed: Nov. 14, 1984

Related U.S. Application Data

[63] Continuation-in-part of Ser. No. 564,965, Dec. 23, 1983, abandoned.

[51] Int. Cl.[4] ............................................... A61K 7/16
[52] U.S. Cl. ........................................................ 424/49
[58] Field of Search ...................................... 424/49-58

[56] References Cited

U.S. PATENT DOCUMENTS

| | | | |
|---|---|---|---|
| Re. 29,182 | 4/1977 | McCune et al. | 424/54 |
| 3,488,419 | 1/1970 | McCune et al. | 424/52 |
| 3,828,977 | 8/1974 | Borchert | 222/95 |
| 3,838,796 | 10/1974 | Cohen | 222/105 |
| 3,925,456 | 12/1975 | Ploger et al. | 260/502.5 |
| 3,934,002 | 1/1976 | Haefele | 424/54 |
| 3,937,807 | 2/1976 | Haefele | 424/52 |
| 3,941,772 | 3/1976 | Ploger et al. | 260/239 B |
| 3,959,458 | 5/1976 | Agricola et al. | 424/52 |
| 3,960,888 | 6/1976 | Ploger et al. | 260/326.5 A |
| 3,988,443 | 10/1976 | Ploger et al. | 424/200 |
| 4,025,616 | 5/1977 | Haefele | 424/52 |
| 4,034,086 | 7/1977 | Ploger et al. | 424/200 |
| 4,042,679 | 8/1977 | Gaffar | 424/54 |
| 4,064,164 | 12/1977 | Blum et al. | 260/502.5 |
| 4,098,880 | 7/1978 | Gaffar | 424/54 |
| 4,100,270 | 7/1978 | Gaffar | 424/54 |
| 4,108,961 | 8/1978 | Ploger et al. | 423/265 |
| 4,108,962 | 8/1978 | Ploger et al. | 423/265 |
| 4,123,512 | 10/1978 | Gaffar | 424/54 |
| 4,137,303 | 1/1979 | Gaffar et al. | 424/52 |
| 4,143,128 | 3/1979 | Kim et al. | 424/54 |
| 4,144,324 | 3/1979 | Crutchfield et al. | 424/54 |
| 4,171,757 | 10/1979 | Diamond | 222/389 |
| 4,177,258 | 12/1979 | Gaffar et al. | 424/52 |
| 4,183,915 | 1/1980 | Gaffar et al. | 424/52 |
| 4,215,105 | 7/1980 | Gaffar et al. | 424/57 |
| 4,224,308 | 9/1980 | Gaffar et al. | 424/49 |
| 4,224,309 | 9/1980 | Gaffar et al. | 424/54 |
| 4,348,381 | 9/1982 | Gaffar et al. | 424/52 |
| 4,353,890 | 10/1982 | Scott | 424/49 |
| 4,419,342 | 12/1983 | Hayes et al. | 424/54 |
| 4,436,721 | 3/1984 | Gaffar | 424/52 |
| 4,474,818 | 10/1984 | Scott | 424/49 |

FOREIGN PATENT DOCUMENTS

115711 9/1981 Japan.
2038303 7/1980 United Kingdom.

*Primary Examiner*—Shep K. Rose
*Attorney, Agent, or Firm*—Robert L. Stone; Murray M. Grill; Herbert S. Sylvester

[57] ABSTRACT

A dentifrice of desirable rheological properties suitable for facile extrusion from a container such as a flexible dentifrice tube or mechanically operated or pressure differential dispenser, which dentifrice comprises a siliceous polishing material, an antinucleating agent containing at least one phosphonic group and a gelling agent mixture of iota-carrageenan and xanthan.

6 Claims, No Drawings

DENTIFRICE

This application is a continuation-in-part of application Ser. No. 564,965, filed Dec. 23, 1983, now abandoned.

This invention relates to a dentifrice. In particular, it relates to a dentifrice having desirable rheological properties such as being a readily extrudable dentifrice from a container, particularly a flexible dentifrice tube or a mechanically operated or pressure differential dentifrice dispenser.

A dentifrice is generally recognizable by its creamy or gel consistency and may commonly be called a dental cream, a toothpaste or, in some cases, a clear gel or opacificed gel toothpaste. Indeed, it can be characterized as a semi-solid, for instance, being essentially solid when standing on the bristles of a toothbrush and essentially liquid such as during manufacture with agitation or when subject to pressure to extrude the dentifrice from its container.

The creamy or gel consistency of dentifrices is imparted by a gelling or binding agent, sometimes supplemented with a non-gelling thickener. In the paste, gelling agents have been selected primarily to provide ease of dispersion of the dentifrice in the oral cavity. Many gelling agents such as cellulosic materials, seaweed derivatives, gums and clays meet this criteria. However, some gelling agents while generally desirable for many dentifrices, do cause problems if some special ingredients, such as antinucleating agents containing at least one phosphonic group are present. For instance, a dentifrice containing a siliceous polishing agent, an ethylene diamine-tetramethylene tetra-phosphonate and a siliceous polishing material with a conventional gelling agent such as sodium carboxymethyl cellulose can become so thick that it cannot even be squeezed out of a flexible dentifrice tube.

Dentifrices containing siliceous polishing agents and conventional gelling agents such as sodium carboxymethyl cellulose or hydroxyethyl cellulose, although often recommended for and used with such dentifrices, have tended to thicken with the passage of time, particularly making such dentifrice difficult to extrude from a mechanically operated or pressure differential dispenser. Kappa carrageenan gelling agent, which has also been recommended, tends to cause such dentifrices to become very thin. Xanthan gelling agent tends to provide desirable rheology (between about 3000 and 6000 dynes/cm$^2$) but causes the dentifrice to be quite soft with limited resiliency. As described in a co-pending application of P. S. Mulvey, J. Barth and L. Vellekoop, filed on even date herewith, i-carrageenan is very desirable as a gelling agent for such dentifrices. However, when an antinucleating agent containing at least one phosphonic group is present too, the dentifrice with i-carrageenan does not possess the required gel character, typically having a viscosity below about 2500 dynes/cm$^2$. The problem is not overcome by mixing i-carrageenan with a cellulosic gelling agent such as sodium carboxymethyl cellulose since electrolytes from the antinucleating agent break down the gel structure.

I-carrageenan has been recommended for dentifrice use for dentifrices packaged in tubes. Indeed, the Copenhagen Pectin Factory, Ltd. of Little Skensved, Denmark, a subsidiary of Hercules, Inc., of Wilmington, Del., U.S.A. has proposed its product Genuvisco Type 0819, an iota-carrageenan (i-carrageenan), as a possible thickener for toothpaste. I-carrageenan available from Marine Colloids Division of FMC Corp. of Springfield, N.J. as Viscarin TP-5 has also been proposed for possible toothpaste use with toothpaste containing dicalcium phosphate or silica. Indeed, i-carrageenan and xanthan have been disclosed as alternatives as a thickener component together with k-carrageenan and alkali metal alginate for a dentifrice containg galactan galactose in Japanese Patent Publication No. 56 115711, published Sept. 11, 1981, of Lion Dentifrice Ltd.

Unexpectedly from amongst alternative types of gelling agents, a mixture of i-carrageenan and xanthan provides excellent extrusion rheology for a dentifrice containing siliceous polishing agent and an antinucleating agent containing at least one phosphonic group, without the breakdown which occurs when i-carrageenan is used alone and without reduced softness of texture which occurs when xanthan is used as the sole gelling agent. It is noteworthy that xanthan has not been compatible with cellulosic gelling agents since it may contain cellulase.

It is an advantage of this invention that a dentifrice is provided which is readily extrudable from a dentifrice container such as a flexible dentifrice tube or a mechanically operated or pressure differential dentifrice dispenser with desirable rheological properties.

Other advantages will be apparent from consideration of the following specification.

In accordance with certain of its aspects, this invention relates to a dentifrice comprising about 20–80% by weight of an aqueous humectant vehicle, about 0.5–5% by weight of gelling agent, about 10–50% by weight of siliceous polishing agent, about 0.01–10% by weight of an antinucleating agent containing at least one phosphonic group, said gelling agent containing about 0.2–2% by weight of the dentifrice of a mixture of i-carrageenan and xanthan in a weight ratio of i-carrageenan to xanthan of about 1:7.5 to about 1:1.5.

In the dentifrice formulation, the dental vehicle comprises a liquid phase proportioned with the gelling agent to form an extrudable creamy mass of desirable consistency. The liquid phase in the dentifrice will comprise chiefly water and humectant such as polyols including glycerine, sorbitol, maltitol, xylitol, low molecular weight polyethylene glycol (e.g. 400 or 600), propylene glycol or the like including suitable mixtures thereof. It is advantageous usually to use as the liquid phase water and a humectant such as glycerine, sorbitol or polyethylene glycol, typically in amounts of about 10–55% by weight of water and about 20–50% by weight of humectant in a dentifrice containing siliceous polishing agent.

Siliceous polishing agent includes an amorphous silica containing combined alumina which can be considered to be an alkali metal aluminosilicate having a refractive index of from 1.44 to 1.47 and containing at least 70% silica, up to 10% alumina, such as about 0.1–10% e.g. about 0.1–3%, preferably up to about 20% of moisture, such as about 0.5–10%; and up to about 10% of alkali metal oxide. Typically, this material has a particle size in the range from 1 to 35 microns, preferably from 2 to 20 microns, e.g. 2 to 4 microns. The preferred moisture content is from 10% to 20% measured by ignition at 1000° C. and the typical content of alkali metal oxide is from 5% to 10%. Generally, the polishing agent has a loose bulk density of up to 0.2 g/cc, such as from 0.07 to 0.12 g/cc.

Another suitable type of polishing agent is porous amorphous silicic anhydride having an average particle size preferably below 20 microns and above 1 micron, a surface area of at least 200 m$^2$/g, preferably at least 300 m$^2$/g, and a bulk density of at least 0.15 g/cm$^3$, preferably at least 0.30 g/cm$^3$, such as a dehydrated silica hydrogel (i.e. a xerogel), preferably of the well known regular density or intermediate density type. Examples of such amorphous silicic anhydride polishing agents are "Syloid 63", "Syloid 72", and "Syloid 74" (SYLOID is a trade mark) which are described in "The Davison Family of Syloid Silicas" published by their manufacturer, Grace, Davison Chemical Company. "Santocel 100" of Monsanto (SANTOCEL is a trade mark), is also a suitable dental abrasive. "Syloid 72" has an average particle size of about 4 microns, a surface area of about 340 m$^2$/g bulk density of about 1.77 g/cm$^3$. For "Syloid 63" the corresponding figures are about 9 microns, about 675 m$^2$/g and about 0.4 g/cm$^3$. A grade of "Santocel 100" has a surface area of about 239 m$^2$/g and a bulk density of about 0.24 g/cm$^3$. These amorphous silicic anhydrides may be used singly or in mixtures.

Hydrous silica which may be used as polishing agent is particularly described in British Published Patent Application No. 2 038 303A of Grace G.m.b.H. The hydrous gel is generally described as having an average particle size of 1 to 30 microns and:

(a) a surface area of 1 to 600 m$^2$/g,
(b) a pore volume of 0.05 to 0.5 cm$^3$/g,
(c) a product of surface area (in m$^2$/g) × pore volume (in cm$^3$/g) less than or equal to 240,
(d) a calculated pore diameter of 1.5 to 2.5 nm, and
(e) a water content of less than 25% by weight.

Polishing agent in the form of synthetic hydrated precipitated silica is not a silica gel, xerogel or aerogel, but is obtained as a finely divided precipitate, such as from a solution of alkali metal silicate and acid. The variables of concentration, pH and temperature are chosen to prevent the formation of a continuous gelatinous mass and to promote the precipitation of silica in a finely divided form which can be readily filtered and washed.

Antinucleating agents containing phosphonic groups have been described in the art as dentifrice components. They may provide desirable anticalculus or antiplaque effect. Typical disclosures are in U.S. Pat. Nos. 4,348,381, 4,224,309 and 4,224,308 each to Gaffar et al; U.S. Pat. No. 4,215,105 to Gaffar et al; U.S. Pat. Nos. 4,183,915 and 4,177,258 to Gaffar et al; U.S. Pat. No. 4,144,324 to Crutchfield et al; U.S. Pat. No. 4,143,128 to Kim et al; U.S. Pat. No. 4,137,303 to Gaffar et al; U.S. Pat. Nos. 4,123,512, 4,100,270, 4,098,880 and 4,042,679 to Gaffar; U.S. Pat. No. 4,064,164 to Blum et al; U.S. Pat. Nos. 4,108,962, 4,108,961, 4,034,086, 3,988,443, 3,960,888, 3,941,772 and 3,925,456 to Ploger et al; U.S. Pat. No. 3,959,458 to Agricola et al; and U.S. Pat. Nos. 4,025,616, 3,937,807 and 3,934,002 to Haefele. Amounts of about 0.01–10% by weight, preferably about 0.1–5% and most preferably about 1–3% of such antinucleating agents can be included in the dentifrice of the present invention. They include acid and non-toxic pharmaceutically acceptable salts (e.g. ammonium and alkali metal, particularly sodium of 2-phosphonobutane tricarboxylic acid -1,2,4;
phosphonoacetic acid;
alkylene diamine tetramethylene phosphonic acids containing 1-10 alkylene groups;
polyalkyl bis-(phosphonomethylene) amine acid;
1,3-di-amino-alkane-1,1-diphosphonic acid as set forth in U.S. Pat. No. 4,064,164;
3-amino-1-hydroxypropane-1,1-diphosphonic acid;
azacycloalkane-2,2-diphosphonic acid containing 4–6 carbon atoms in the heterocyclic ring;
pyrrolidone-5,5-diphosphonic acid wherein the hetero-N atom is substituted with hydrogen or an alkyl group containing 1–6 carbon atoms;
azacycloalkane-2,2-diphosphonic acid wherein the hetero-N atom is substituted with hydrogen or an alkyl group containing 1–3 carbon atoms and containing 4–6 carbon atoms in the hetrocyclic ring;
2-hydroxy-2-oxo-3-amino-3-phosphonyl-5-oxo-1-aza-2-phospha-cycloalkanes as set forth in U.S. Pat. No. 3,925,456;
anticalculus agents of U.S. Pat. No. 3,959,458 typified by ethane-1-hydroxy-1,1-diphosphonic acid.

Alkylene diamine tetramethylene phosphonic salts, particularly sodium salts of ethylene diamine tetramethylene phosphonic acid are preferred.

The gelling agent of the present invention is present in the dentifrice amount of about 0.2–2% by weight. I-carrageenan mixed with xanthan in a weight ratio of from 1:7.5 to about 1:1.5, preferably from about 1:4 to about 1:2.5. The yield point viscosity of a dentifrice containing the mixed gel system in accordance with the invention typically is about 3000–5000 dynes/cm$^2$, preferably about 3500–4500 dynes/cm$^2$ (measured on Haake Rotovisco RV3 Viscometer using a profiled cup).

As mentioned above, iota carrageenan is commercially available as Genuvisco type 0819 and Viscarin TP-5 and has been recommended for use in a toothpaste. Such use in a toothpaste was described in Japanese Patent Publication No. 56 115711 of Lion Dentifrice Ltd., wherein i-carrageenan and xanthan are mentioned as alternative possible components of a gelling system together with k-carrageenan and alkali metal alginate. In U.S. Pat. No. 4,353,890 to Scott, i-carrageenan is disclosed as an alternative to k-carrageenan as a toothpaste gelling agent wherein the toothpaste is subjected to microwave radiation to reduce the tendency of carrageenan in general to become thin during manufacture. The carrageenan may be sole gelling agent or mixed with other gelling agents. In the present invention, dentifrice containing i-carrageenan does not require microwave radiation.

The prior art generally discussed above does not indicate that gelling systems based on i-carrageenan and xanthan can provide dentifrices containing siliceous polishing agent and antinucleating agent containing at least one phosphonic group with the rheology necessary for long-term extrusion from a flexible dentifrice tube or a mechanically operated or pressure differential dispenser.

It is noteworthy that U.S. Pat. No. 4,029,760 to de Roeck et al disclosed an oral composition in which i-carrageenin is set forth as an antigingivitis agent alternative to other carrageenins. Carrageenins are highly depolymerized derivatives of carrageenans. Carrageenans do not appear to provide an antigivitis effect.

Dentifrices are commonly manufactured by a cold process, e.g. at about 25° C., or by a hot process, e.g. at about 60° C. I-carrageenan can be used in either cold process or hot process techniques. Since xanthan is made with cold processing, the two gelling agents may be readily mixed and incorporated into the dentifrice together. K-carrageenan can only be used with hot processing.

Physical properties of Genuvisco type 0819 i-carrageenan are indicated below:

1. Viscosity of 0.30% solution of GENUVISCO type 0819 in lean solvent prepared using a hot process (60° C.):
   Viscosity=690±80 cP measured on Brookfield Viscometer LVT at 25° C.
   Viscosity=110±17 cP at 32 rpm.
   Viscosity=70±11 cP at 64 rpm.
   Viscosity=45±7 cP at 128 rpm.
   Measured on HAAKE Rotovisco RV3 at 25° C.
2. Viscosity of 0.30% solution of GENUVISCO type 0819 in lean solvent prepared using a cold process (25° C.):
   Viscosity=450±60 cP measured on Brookfield Viscometer LVT at 25° C.
   Viscosity=85±13 cP at 32 rpm.
   Viscosity=55±8 cP at 64 rpm.
   Viscosity=37±6 cP at 128 rpm.
   Measured on HAAKE Rotovisco RV3 at 25° C.
3. Particle size: Less than 1% gum on 0.075 mm test sieve (DIN 80, 200 US mesh).
4. Moisture content: Less than 12%.
5. pH: 8.5±1.5 in 0.5% solution in distilled water at 25° C.
6. Color: White to cream.

Viscarin TP-5 i-carrageenan has the following physical properties:
Color: light tan to tan.
Particle size: more than 95.0% through a U.S. Standard Sieve, 250 nm (Series #60)
Moisture: maximum 12.0% (Cenco Moisture Balance).
pH: 7.0 to 9.5, 1.5% solution, 30° C. 86° F.).

Xanthan gum is a fermentation product prepared by action of the bacteria of the genus Xanthomonas upon carbohydrates. Four species of Xanthomonas, viz *X. campetris. X. phaseoli, X. malvocearum,* and *X. carotae* are reported in the literature to be the most efficient gum procedures. Although the exact chemical structure is not determined, it is generally accepted to be a heteropolysaccharide with a molecular weight of several million. It contains D-glucose, D-mannose, and D-glucuronic acid in the molar ratio of 2.8:3.2.0. The molecule contains 4.7% acetyl and about 3% pyruvate. The proposed chemical structure configuration can be found in McNeely and Kang, Industrial Gums, ed. R. L. Whistler, CH XXI, 2nd Edition, New York, 1973. The procedure for growing, isolating and purifying the xanthan gum is also found in that publication. Further description of xanthan gum is found in Manufacturing Chemist, May 1960, pages 206–208 (including mention at page 208 of potential use of gums therein described for formulating toothpastes).

Synthetic finely divided silicas such as those sold as the "Cab-O-Sil M-5", "Syloid 244", "Syloid 266", "Aerosil D200" and mixtures thereof, may also be employed, e.g. in amounts of from 0.5% to 20% by weight, preferably about 5–10%, to promote thickening of the dentifrice.

The dentifrice is packaged in a container from which it can be readily extruded such as a pressure differential or mechanically operated dental cream dispenser or a lined or unlined aluminium tube or wax lined lead tube or plastic tube, which may be laminated with aluminum. The rheological properties are highly desirable when a mechanically operated dispensing container of the type described in British patent application No. 2,070,695A, published Sept. 9, 1981, is employed. This dispensing container comprises a dispensing mouthpiece, a tension member, a central rod, a piston and operating hand control. The disclosure of this published application is incorporated herein by reference.

Pressure differential dispensing container may be of the aerosol or vacuum type. Suitable pressure differential dispensers include those comprising a collapsible product-containing bag being disposed within a rigid container which contains a propellant fluid. In such dispensing containers, operation of the valve permits release of the product only, the propellant fluid being separated from the product by the fluid impermeable bag. Dispensers of this type are described in U.S. Pat. Nos. 3,828,977 and 3,838,796. These are the so-called Sepro dispensers. So-called Exxel containers also utilize pressure.

Still another type dispenser is the barrier piston container described in U.S. Pat. No. 4,171,757. Such container includes a valve, a product-containing compartment and an essentially fluid-tight barrier piston which separates the propellant fluid from the contained product (The so-called Diamond container.)

The dentifrice may contain a compound which provides at least about 100 ppm, of fluoride, typically about 100–10000 ppm, typically about 750–2000 ppm. Compounds which provide fluorine include sodium fluoride, stannous fluoride, potassium fluoride, potassium stannous fluoride, sodium hexafluorostannate, stannous chlorofluoride, sodium monofluorophosphate and amine fluorides including mixtures thereof. Most typically in accordance with the present invention sodium fluoride, sodium monofluorophosphate or a mixture of sodium monofluorophosphate and sodium fluoride may be employed.

The dentifrice may preferably contain sodium fluoride or sodium monofluorophosphate or a mixture of sodium monofluorophosphate and sodium fluoride in amount to provide about 100–10000 ppm of fluorine, e.g. about 750–2000 ppm, and particularly about 1400–2000 ppm such as about 1400–1670 ppm. A binary fluoride system of sodium monofluorophosphate and sodium fluoride is desirably used in which about 30–40% of the fluorine (e.g. about 30–35%) is provided by sodium fluoride.

Sodium monofluorophosphate, $Na_2PO_3F$, as commercially available may vary considerably in purity. It may be used in any suitable purity provided that any impurities do not substantially adversely affect the desired properties. In general, the purity is desirably at least 80%. For best results, it should be at least 85%, and preferably at least 90% by weight of sodium monofluorophosphate with the balance being primarily impurities or by-products of manufacture such as sodium fluoride and water-soluble sodium phosphate salt. Expressed in another way, the sodium monofluorophosphate employed should have a total fluoride content of above 12%, preferably above 12.7%, a content of not more then 1.5%, preferably not more than 1.2% of free sodium fluoride; and a sodium monofluorophosphate content of at least 12%; preferably at least 12.1% all calculated as fluoride.

As indicated above, sodium fluoride in the binary mixture is a separate fluorine-containing component from sodium monofluorophosphate. About 225–800 ppm of fluorine is preferably provided to the dental cream by sodium fluoride.

Any suitable surface active or detersive material may be included in the dentifrice compositions. Such compatible materials are desirable to provide additional detersive, foaming and anti-bacterial properties depending upon the specific type of surface active material and are selected similarly. These detergents are water-soluble compounds usually, and may be anionic, nonionic, or cationic in structure. It is usually preferred to use the water-soluble non-soap or synthetic organic detergents. Suitable detersive materials are known and include, for example, the water-soluble salts of higher fatty acid monoglyceride monosulphate detergent (e.g., sodium coconut fatty acid monoglyceride monosulphate), higher alkyl sulphate (e.g. sodium lauryl sulphate), alkyl aryl sulphonate (e.g. sodium dodecyl benzene sulphonate, higher fatty acid esters of 1,2-dihydroxy propane sulphonate) and the like.

Further surface active agents include the substantially saturated higher aliphatic acyl amides of lower aliphatic amino carboxylic acid compounds, such as those having 12 to 16 carbons in the acyl radical. The amino acid portion is derived generally from the lower aliphatic saturated monoaminocarboxylic acids having about 2 to 6 carbons, usually the monocarboxylic acid compounds. Suitable compounds are the fatty acid amides of glycine, sarconsine, alanine, 3-aminopropanoic acid and valine having about 12 to 16 carbons in the acyl group. It is preferred to use the N-lauroyl, myristoyl and palmitoyl sarcoside compounds, however, for optimum effects.

The amide compounds may be employed in the form of the free acid or preferably as the water-soluble salts thereof, such as the alkali metal, ammonium, amine and alkylolamine salts. Specific examples thereof are the sodium and potassium N-lauroyl, myristoyl and palmitoyl sarcosides, ammonium and ethanolamine N-lauroyl glycide and alanine. For convenience herein, reference to "amino carboxylic acid compound", "sarcoside", and the like refers to such compounds have a free carboxylic group of the water-soluble carboxylate salts.

Such materials are utilized in pure or substantially pure form. They should be as free as practicable from soap or similar higher fatty acid material which tends to reduce the activity of these compounds. In usual practice, the amount of such higher fatty acid materials is less that 15% by weight of the amide and insufficient to substantially adversely affect it, and preferably less than about 10% of said amide material.

Various other materials may be incorporated in the dentifrices of this invention. Examples thereof are colouring or whitening agents, preservatives, such as methyl p-hydroxybenzoate or sodium benzoate, stabilisers, silicones, chlorophyll compounds and ammoniated materials such as urea, diammonium phosphate and mixtures thereof. These adjuvants are incorporated in the instant compositions in amount which do not substantially adversely affect the desired properties and characteristics and are suitably selected and used in conventional amounts.

For some purposes it may be desirable to include antibacterial agents in the compositions of the present invention. Typical antibacterial agents which may be used in amounts of about 0.01% to about 5%, preferably about 0.05% to about 1.0%, by weight of the dentifrice composition include:

$N^1$-4(chlorobenzyl)-$N^5$-(2,4-dichlorobenzyl)biguanide;
p-chlorophenyl biguanide;
4-chlorobenzhydryl biguanide;
4-chlorobenzhydrylguanylurea;
N-3-lauroxypropyl-$N^5$-p-chlorobenzylbiguanide;
1,6-di-p-chlorophenylbiguanidehexane;
1-(lauryldimethylammonium)-8-(p-chlorobenzyldimethylammonium)octane dichloride;
5,6-dichloro-2-guanidinobenzimidazole;
$N^1$-p-chlorophenyl-$N^5$-laurylbiguanide;
5-amino-1,3-bis(2-ethylhexyl)-5-methylhexahydropyrimidine;
and their non-toxic acid addition salts.

Any suitable flavouring or sweetening materials may be employed in formulating a flavour for the compositions of the present invention. Examples of suitable flavouring constituents include the flavouring oils, e.g., oils of spearmint, peppermint, wintergreen, sassafras, clove, sage, eucalyptus, marjoram, cinnamon, lemon and orange, as well as methylsalicylate. Suitable sweetening agents include sucrose, lactose, maltose, sorbitol, sodium cyclamate, sodium saccharine dipeptides of U.S. Pat. No. 3,939,261 and oxathiazin salts of U.S. Pat. No. 3,932,606. Suitable flavour and sweetening agent may together comprise from about 0.01 to 5% or more of the composition.

The dentifrices should have a pH practicable for use. A pH range of 5 to 9 is particularly desirable. The reference to the pH is meant to be the pH determination directly on the dentifrice. If desired, materials such as benzoic, or citric acid may be added to adjust the pH to, say 5.5 to 6.5.

The following examples are further illustrative of the nature of the present invention, but it is to be understood that the invention is not limited thereto. All amounts of the various ingredients are by weight unless otherwise specified.

EXAMPLE 1

The following dentifrice is prepared:

|  | PARTS |
| --- | --- |
| Glycerine | 25.00 |
| Xanthan (Keltrol) | 1.10 |
| I-Carrageenan (Genuvisco 0819) | 0.20 |
| Sodium saccharin | 0.20 |
| Sodium benzoate | 0.50 |
| Titanium dioxide | 0.40 |
| Sodium fluoride | 0.22 |
| Ethylene diamine-tetramethylene tetraphosphonic acid, sodium salt | 2.75 |
| Amorphous silica containing about 1% combined alumina (Zeo 49-Huber) | 27.00 |
| Sodium lauryl sulphate | 1.50 |
| Flavour | 1.00 |
| Deionized water | 40.13 |
| pH | 6.9 |

The dentifrice sets well to a creamy consistency and is extruded well from a flexible plastic lined aluminium tube, a mechanically operated dispenser and a pressure differential dispenser. After 1 week it was a desirable yield point viscosity of 3400 dynes/cm$^2$, measured on a Haake Rotovisco RV3 Viscometer using a profiled cup.

When the above dentifrice is modified to use 1.30 parts of i-carrageenan in place of the mixture of i-carrageenan and xanthan the dentifrice loses its consistency, becomes highly liquid and falls apart.

EXAMPLE 2

The dentifrice of Example 1 is modified to contain 1.10 parts of xanthan and 0.40 parts of i-carrageenan with a corresponding reduction in the amount of deionized water to 39.93 parts. The pH is 6.7.

The rheology including consistency and extrusion characteristic from a plastic lined aluminum tube, a mechanically operated dispenser and a pressure differential dispenser is quite good. The yield point viscosity 1 week after preparation is highly desirable, 3750 dynes/cm$^2$, measured on a Haake Rotovisco RV3 Viscometer using a profiled cup.

In the dentifrices of the above examples, similar rheological results can be obtained on replacing ethylene diamine tetramethylene tetraphosphonate salt with other antinucleating agents containing at least one phosphonic group including sodium salts of 2-phosphonobutane tricarboxylic acid-1,2,4 and ethane-1-hydroxy-1,1-diphosphonic acid.

It will be apparent to those skilled in the art that further modifications of the examples illustrative of the invention, may be made thereto.

I claim:

1. A dentifrice comprising about 0.5–5% by weight of gelling agent, about 20–80% by weight of aqueous humectant vehicle, about 10–50% by weight of siliceous polishing agent, selected from the group consisting of amorphous silica containing combined alumina, porous amorphous silicic anhydride, hydrous silica and synthetic hydrated precipitated silica, about 0.01–10% by weight of an antinucleating agent which provides an anticalculus or antiplaque effect containing at least one phosphonic group, said gelling agent containing about 0.2–2% by weight of the dentifrice of a mixture of i-carrageenan and xanthan in a weight ratio of i-carrageenan to xanthan of about 1:7.5 to about 1:1.5.

2. The dentifrice claimed in claim 1 wherein said weight ratio is from about 1:4 to about 1:2.5.

3. The dentifrice claimed in claim 1 wherein said polishing agent is an amorphous silica containing combined alumina.

4. The dentifrice claimed in claim 3 wherein said antinucleating agent is a water-soluble non-toxic salt of ethylene diamine tetramethylene tetraphosphonic acid.

5. The dentifrice claimed in claim 4 wherein said antinucleating agent is present in amount of about 0.1–5% by weight.

6. The dentifrice claimed in claim 1 wherein said antinucleating agent is a water-soluble non-toxic salt of ethylene diamine tetramethylene tetraphosphonic acid, 2-phosphonobutane tricarbonoxylic acid-1,2,4 or ethane-1-hydroxy-1,1-diphosphonic acid.

* * * * *